(12) United States Patent
Karim et al.

(10) Patent No.: US 9,669,393 B2
(45) Date of Patent: Jun. 6, 2017

(54) CATALYST FOR SELECTIVE SYNTHESIS OF LOWER HYDROCARBONS FROM SYNGAS

(71) Applicant: SAUDI BASIC INDUSTRIES CORPORATION, Riyadh (SA)

(72) Inventors: Khalid Karim, Riyadh (SA); Saleh Al-Sayaria, Riyadh (SA); Graham Hutchings, Herefordshire (GB); Sarwat Iqbal, Cardiff (GB)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/785,982

(22) PCT Filed: Apr. 22, 2014

(86) PCT No.: PCT/IB2014/001427
§ 371 (c)(1),
(2) Date: Oct. 21, 2015

(87) PCT Pub. No.: WO2014/174374
PCT Pub. Date: Oct. 30, 2014

(65) Prior Publication Data
US 2016/0067684 A1    Mar. 10, 2016

Related U.S. Application Data

(60) Provisional application No. 61/815,393, filed on Apr. 24, 2013.

(51) Int. Cl.
| | | |
|---|---|---|
| *B01J 27/051* | (2006.01) |
| *C10G 2/00* | (2006.01) |
| *C07C 1/04* | (2006.01) |
| *B01J 37/03* | (2006.01) |
| *B01J 21/16* | (2006.01) |
| *B01J 23/00* | (2006.01) |

(52) U.S. Cl.
CPC ........... *B01J 27/0515* (2013.01); *B01J 21/16* (2013.01); *B01J 23/002* (2013.01); *B01J 37/031* (2013.01); *C07C 1/0435* (2013.01); *C10G 2/332* (2013.01); *C10G 2/334* (2013.01); *B01J 2523/00* (2013.01); *C07C 2521/06* (2013.01); *C07C 2523/06* (2013.01); *C07C 2523/28* (2013.01); *C07C 2523/75* (2013.01); *C07C 2523/755* (2013.01); *C07C 2527/02* (2013.01)

(58) Field of Classification Search
CPC .... B01J 27/0515; B01J 37/031; B01J 23/002; B01J 2523/47; B01J 2523/48; B01J 2523/62; B01J 2523/68; B01J 2523/845; B01J 2523/847; C10G 2/334; C10G 2/332; C07C 1/0435; C07C 2523/75; C07C 2523/755; C07C 2521/06; C07C 2521/08; C07C 2523/28; C07C 2523/06; C07C 2527/02; Y02P 20/52

USPC .......................................... 502/216, 220–222
See application file for complete search history.

(56) References Cited

U.S. PATENT DOCUMENTS

| | | | | |
|---|---|---|---|---|
| 2,325,033 A | * | 7/1943 | Byrns | ................. B01J 23/882 208/216 R |
| 3,884,834 A | * | 5/1975 | Eberly | ................. B01J 23/26 502/220 |
| 4,039,302 A | | 8/1977 | Khera | |
| 4,451,579 A | | 5/1984 | Lemanski et al. | |
| 4,491,639 A | * | 1/1985 | Happel | ................. B01J 27/02 502/204 |
| 4,752,623 A | | 6/1988 | Stevens et al. | |
| 4,902,404 A | * | 2/1990 | Ho | ................. C10G 65/04 208/228 |
| 4,929,585 A | * | 5/1990 | Lee | ................. B01J 27/047 502/216 |
| 4,937,221 A | | 6/1990 | Erekson et al. | |
| 4,956,327 A | * | 9/1990 | Erekson | ................. B01J 23/00 502/216 |
| 4,973,397 A | * | 11/1990 | Ho | ................. B01J 31/1616 208/112 |

(Continued)

FOREIGN PATENT DOCUMENTS

| | | |
|---|---|---|
| CN | 1036710 A | 11/1989 |
| CN | 102574110 A | 7/2012 |

(Continued)

OTHER PUBLICATIONS

International Search Report and Written Opinion issued by the International Searching Authority on Dec. 15, 2014 for international application PCT/IB2014/001427, filed on Apr. 22, 2014 and published as WO 2014/174374 on Oct. 30, 2014 (Applicant—Saudi Basic Industries Corporation // Inventor—Karim, et al.) (9 pages).

*Primary Examiner* — Patricia L Hailey
(74) *Attorney, Agent, or Firm* — Ballard Spahr LLP

(57) ABSTRACT

The present disclosures and inventions relate to a catalyst composition for the selective conversion of a hydrogen/carbon monoxide mixture (syngas) to $C_1$-$C_5$ hydrocarbons, wherein the catalyst composition, which can be optionally dispersed on a support material, has the formula $CO_aMO_b$-$S_cM_dO_f$, wherein a is 1; wherein b is from 0.8 to 1.2; wherein c is from 1 to 2; wherein M comprises Zn, Ti, Zr, or Ni, or a mixture thereof, wherein d is from 0.000001 to 0.2; and wherein f is a number determined by the valence requirements of the other elements present in the catalyst.

20 Claims, No Drawings

(56) References Cited

U.S. PATENT DOCUMENTS

| | | |
|---|---|---|
| 6,160,162 A | 12/2000 | Karim et al. |
| 7,253,136 B2 | 8/2007 | Mauldin et al. |
| 7,365,040 B2 | 4/2008 | Van Berge et al. |
| 7,375,055 B2 | 5/2008 | Van Berge et al. |
| 8,834,710 B2 * | 9/2014 | Domokos .............. B01J 23/883 208/145 |
| 2004/0152586 A1 * | 8/2004 | Ou ........................ B01J 23/002 502/64 |
| 2005/0059545 A1 * | 3/2005 | Alonso .................. B01J 27/051 502/220 |
| 2008/0033218 A1 | 2/2008 | Lattner et al. |
| 2010/0331581 A1 | 12/2010 | Kharas et al. |

FOREIGN PATENT DOCUMENTS

| | | |
|---|---|---|
| EP | 0187102 A1 | 7/1986 |
| WO | WO-00/29106 A1 | 5/2000 |
| WO | WO-2009/032982 A2 | 3/2009 |
| WO | WO-2010/077860 A2 | 7/2010 |
| WO | WO-2012/143131 A1 | 10/2012 |
| WO | WO-2013/007345 A1 | 1/2013 |

* cited by examiner

CATALYST FOR SELECTIVE SYNTHESIS OF LOWER HYDROCARBONS FROM SYNGAS

CROSS-REFERENCE TO RELATED APPLICATIONS

This is a U.S. National Phase Application of International Application No. PCT/IB2014/001427, filed Apr. 22, 2014, which claims the benefit of U.S. Provisional Application No. 61/815,393, filed on Apr. 24, 2013, which are both incorporated herein by reference in their entirety.

FIELD OF THE INVENTIONS

The compositions and methods disclosed herein relate to catalyst compositions for the conversion of hydrogen/carbon monoxide mixtures (syngas) to hydrocarbons.

BACKGROUND

Syngas (mixtures of hydrogen and carbon monoxide) can be readily produced from either coal or methane (natural gas) by methods well known in the art and widely commercially practiced around the world. A number of well-known industrial processes use syngas for producing various oxygenated organic chemicals. The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprised iron or cobalt supported on alumina or titania, and promoters, like rhenium, zirconium, manganese, and the like were sometimes used with cobalt catalysts, to improve various aspects of catalytic performance. The products were typically gasoline-range hydrocarbon liquids having six or more carbon atoms, along with heavier hydrocarbon products.

More recently however, the Fischer-Tropsch process has been increasingly focused on and developed as methods for preparing the heavier hydrocarbons suitable for use as diesel fuels, and/or waxy hydrocarbon molecules suitable for conversion to clean, efficient lubricants.

In modern oil refineries, lower molecular weight $C_1$-$C_5$ hydrocarbons (paraffins and/or olefins) are typically obtained in limited amounts from natural gas condensates and/or petroleum distillates, and are in high demand for conversion (by well-known refinery processes such as steam cracking) to high value lower olefins such as ethylene, propylene, and butenes, which are used in many types of applications, especially as monomers for making plastics.

Accordingly, there remains a long-term market need for new and improved methods for producing increased amounts of lower molecular weight $C_1$-$C_5$ hydrocarbons from non-petroleum feedstocks. Catalysts and methods useful for the production of $C_1$-$C_5$ hydrocarbons from syngas are described herein.

SUMMARY OF THE INVENTION

Described herein are catalysts, wherein the catalysts comprise components according to the formula $$Co_aMo_bS_cM_dO_f.$$

wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2; and
wherein f is a number determined by the valence requirements of the other elements present in the catalyst.

Also provided are methods for preparing the catalyst compositions of the inventions comprising the steps of
a) providing a solution comprising Mo and S;
b) providing a solution comprising Co;
c) mixing the solution comprising Mo and S with the solution comprising Co, thereby forming $CoMoS_2$;
d) providing a solution comprising M, wherein M comprises Zn, Ti, Zr, or Ni, or a mixture thereof;
e) mixing the solution comprising M with the $CoMoS_2$, and
f) isolating the catalyst composition as a solid.

In yet another aspect, described herein are methods for producing $C_1$-$C_5$ hydrocarbons comprising contacting syngas with a reduced form of a catalyst composition comprising $$Co_aMo_bS_cM_dO_f.$$

wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2;
wherein f is a number determined by the valence requirements of elements of the other elements present in the catalyst composition, and
wherein the method produces $C_1$-$C_5$ hydrocarbons.

The methods for producing $C_1$-$C_5$ hydrocarbons from syngas described herein typically and unexpectedly provide high conversions of the syngas, yet are unexpectedly selective for the production of low molecular weight $C_1$-$C_5$ hydrocarbons, and produce very few or no $C_6$ or higher hydrocarbons, waxes, alcohols, or the like.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to ["an aromatic compound" includes mixtures of aromatic compounds, reference to "a pharmaceutical carrier" includes mixtures of two or more such carriers, and the like].

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges can be expressed herein as from " " one particular value, and/or to " " another particular value. When such a range is expressed, another aspect includes from the one particular value and/or to the other particular value. Similarly, when values are expressed as approximations, by use of the antecedent "," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

As used herein, the terms space time yield ("STY") refers to the tons or kg of product that is produced per unit time per volume of catalyst.

1. Catalysts For Selectively Converting Syngas to Hydrocarbons

Described herein are catalyst compositions for selectively converting syngas to hydrocarbons, wherein the catalyst composition at least comprises components according to the formula

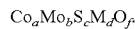

wherein a is 1;
wherein b is from 0.8 to 1.2;
wherein c is from 1 to 2;
wherein M comprises Zn, Ti, Zr, or Ni, or a mixture thereof, wherein d is from 0.000001 to 0.2; and
wherein f is a number determined by the valence requirements of the other elements present in the catalyst.

The $Co_aMo_bS_cM_dO_f$ compositions described herein can be prepared by modifying $CoMoS_2$, as described herein below, or by other methods, then exposing the composition to syngas at elevated temperatures. Such exposure produces a reduced form of the catalyst composition. The introduction of Metal atoms or ions "M" onto or into solid $CoMoS_2$ can occur during the synthesis of the modified solids as described elsewhere herein. Partial substitution of the sulfur atoms or ions with oxygen can occur during the synthetic procedures, or when the modified solid is contacted with syngas at elevated temperatures characteristic of the conversion of syngas to hydrocarbons.

The $Co_aMo_bS_cM_dO_f$ catalyst compositions described herein can be non-stoichiometric solids, i.e. single phase solid materials whose composition cannot be represented by simple ratios of well-defined simple integers, because those solids probably contain solid state point defects (such as vacancies or interstitial atoms or ions) that can cause variations in the overall stoichiometry of the composition. Such phenomena are well known to those of ordinary skill in the arts related to solid inorganic materials, especially for transition metal oxides and sulfides. Accordingly, for convenience and the purposes of this disclosure, the composition of the potentially non-stoichiometric catalytically active solids described herein will be quoted in ratios of moles of the other atoms as compared to the moles of cobalt ions or atoms in the same composition, whatever the absolute concentration of cobalt present in the composition. Accordingly, for purposes of this disclosure, the value of "a" will be assumed to be 1 (one), regardless of the absolute concentration of cobalt in the catalyst composition, and the subscript numbers for the other elements representing the molar ratios that need not be integer ratios.

In the $Co_aMo_bS_cM_dO_f$ catalyst compositions described herein, the molar ratio of molybdenum atoms to cobalt atoms, i.e. the value of "b" in the formulas for the composition, can be from 0.8 to 1.2, or from 0.9 to 1.1, varying somewhat on the presence and quantity of the additional transition metal atoms or ions "M". In one aspect, b can be 1.

During the synthesis of the $Co_aMo_bS_cM_dO_f$ catalyst compositions described herein, the quantity of sulfur atoms or ions that were initially present in the "parent" solid $CoMoS_2$, can vary and/or change significantly, so that the molar coefficient "c" representing the relative quantity of sulfur in the final composition can range from 1 to 2, or from 1 to 1.5. In one aspect, c can be 1.

"M" can be a transition metal atom or ion selected from Zn, Ti, Zr, or Ni, or a mixture thereof, and can be present in molar ratios as compared to cobalt corresponding to a coefficient "d" from 0.0001 to 0.2, or from 0.001 to 0.01, or from 0.004 to 0.01. In one aspect, M can be Zn. In another aspect, M can be Ti. In yet another aspect, M can be Ni.

In the $Co_aMo_bS_cM_dO_f$ catalyst compositions described herein, the molar ratio of oxygen atoms to cobalt atoms, i.e. the value of the coefficient "f" can be a number determined stochiometrically depending on the values of the other components in the catalyst composition. In one aspect, the value of f can be any whole integer or decimal fraction between 0 and 10. In some aspects of the catalysts described herein, f is greater than zero. In some aspects of the catalysts described herein, f can be from 1 to 5.

In one aspect, f can be 0 (zero). Even though a suitable catalyst composition of these inventions may be prepared or loaded into a reactor in the form of a mixed oxide (i.e. f is initially greater than 0), contact with hot syngas, either before or during the catalytic conversion of syngas to hydrocarbons begins, may result in the "in-situ" reduction of the catalyst composition and/or partial or complete removal of oxygen from the solid catalyst composition, with the result that f can be decreased to zero or zero.

In one aspect, $Co_aMo_bS_cM_dO_f$ can be optionally dispersed on or onto a catalyst support material, a binder, a filler, and/or a lubricant, and are shown herein below to be active for the selective conversion of syngas to $C_1$-$C_5$ hydrocarbons.

In another aspect, $Co_aMo_bS_cM_dO_f$ can be optionally dispersed on or onto a catalyst support material. Many such support materials are well known to those of ordinary skill in the art. They are typically catalytically inert, but typically provide physical support, strength and integrity to catalyst particles or pellets containing both the catalyst compositions and the support material, so that catalyst lifetimes are improved. Suitable support materials for the catalyst compositions described herein include clays, $Al_2O_3$, $SiO_2$, $TiO_2$, $CeO_2$, $AlPO_4$, $ZrO_2$, silicon-carbide, Molybdenum-carbide, alumino-silicates, zeolites, molecular sieves, and mixtures thereof, or as separate components.

In yet another aspect, $Co_aMo_bS_cM_dO_f$ can be optionally dispersed on or onto a binder. Binders are typically inert inorganic oxides or clays that are resistant to the high temperature and other conditions of the processes described herein, but physically bind the zeolite particles together and/or increase their resistance to mechanical attrition. Often, the treated zeolite and the binder are mixed in a liquid solvent, then formed or molded into suitable shapes for catalyst pellets, such as pellets or tablets, then the liquid is removed and the catalyst pellet calcined, via methods known to those of ordinary skill in the art. The binders serve to provide physical integrity and mechanical strength to the catalyst particles. Suitable inorganic binders include alumina, silica, titania, zirconia, or magnesia, and suitable clays including montmorillonite and kaolin clays, and mixtures thereof. In some aspects, the catalyst binder is an alumina. In some aspects, the catalyst binder is silica. In some aspects, the catalyst binder is titania. In some aspects, the catalyst binder is zirconia. In some aspects, the catalyst binder is magnesia. In some aspects, the catalyst binder is clay.

In yet another aspect, $Co_aMo_bS_cM_dO_f$ can be optionally dispersed on or onto a filler. Suitable fillers include silicate or alumino-silicate clays, such as bentonite or montmorillonite clays.

In yet another aspect, $Co_aMo_bS_cM_dO_f$ can be optionally dispersed on or onto $K_2CO_3$.

In yet another aspect, $Co_aMo_bS_cM_dO_f$ can be optionally dispersed on or onto a lubricant. Lubricants are used to aid the formation of large composite particles or tablets from mixtures of the catalyst composition and supports and/or binders. Suitable lubricants include Sterotex, a powder comprising waxy hydrogenated vegetable oils available from ABITECH of Janesville Wis.

2. Methods for Preparing the Catalyst

Also disclosed herein are methods for preparing a catalyst comprising the steps of:
a) providing a solution comprising Mo and S;
b) providing a solution comprising Co;
c) mixing the solution comprising Mo and S with the solution comprising Co, thereby forming $CoMoS_2$;
d) providing a solution comprising M, wherein M comprises Zn, Ti, Zr, or Ni, or a mixture thereof; and
e) mixing the solution comprising M with the $CoMoS_2$, to form a catalyst.

In this solution phase method for preparing the catalyst compositions described herein, the first step of the method relates to providing a solution comprising Mo (molybdenum atoms or ions) and S (sulfur atoms or ions). In one aspect, this step can involve dissolving a compound already comprising Mo and S in a suitable solvent. Many compounds comprising Mo and/or S that are soluble in suitable solvents can be suitable and are known to those of ordinary skill in the art. In one aspect, water or low molecular weight alcohols, or mixtures thereof can be suitable solvents.

Alternatively, in other aspects of the methods for preparing the catalyst compositions, the "providing" step can be performed by dissolving separate compounds comprising Mo and S in a single solvent wherein they separately dissolve, or the two compounds separately comprising Mo and S can be dissolved in a solvent and react, to generate a single compound comprising both Mo and S. Examples of a suitable single compound comprising both Mo and S are salts of $MoS_4^{2-}$ (thiomolybdate, such as ammonium thiomolybdate). One such suitable method for this "providing" step is described in the Examples below, where ammonium molydate tetrahydrate $[(NH_4)_6Mo_7O_{24}4H_2O]$ is dissolved into a pre-prepared 20% aqueous solution of ammonium sulfide $[(NH_4)_2S/H_2O]$, and the molybdate and sulfide compounds react to form an aqueous solution of ammonium thiomolybdate, $(NH_4)_2MoS_4$, a solution that comprises both Mo and S.

The second step of the methods for preparing the catalyst compositions described herein relates to providing a solution comprising Co (cobalt atoms or ions). Many suitable compounds comprising Co that are soluble in suitable solvents can be suitable and are known to those of ordinary skill in the art. In one aspect, water or low molecular weight alcohols, or mixtures thereof can be suitable solvents for this step. Any cobalt (II) or (III) salt that is soluble in water can be used, and the use of cobalt (II) acetate, $[Co(CH_3CO_2)_2]$, (commercially available from Sigma-Aldrich as a tetrahydrate) is a specific example of a suitable Co compound that can be dissolved to provide a suitable solution comprising Co.

The third step of the methods for preparing the catalyst compositions described herein relates to mixing the solution comprising Mo and S with the solution comprising Co, to provide a compound comprising Mo, S, and Co, such as, for example, but not limited to $CoMoS_2$. Example 1 describes such a third reaction step, involving the simultaneous addition of aqueous solutions of ammonium thiomolybdate, $(NH_4)_2MoS_4$, and cobalt (II) acetate, $[Co(CH_3CO_2)_2]$, into liquid acetic acid, a step which results in the formation and at least partial precipitation of $CoMoS_2$ as a black solid, which can be collected by filtration and initially dried in air, then dried at high temperatures under nitrogen gas.

The fourth, and fifth steps of the methods for preparing the catalyst compositions of the inventions described above relates to
d) providing a solution comprising M, wherein M comprises Zn, Ti, Zr, or Ni, or a mixture thereof; and
e) mixing the solution comprising M with the $CoMoS_2$, to form a catalyst.

Step "d" involves preparing a solution of one or more suitable compounds comprising Zn (zinc atoms or ions), Ti (titanium atoms or ions), Zr (zirconium atoms or ions), or Ni (nickel atoms or ions), or a mixture thereof in a suitable solvent. Many suitable compounds comprise Zn, Ti, Zr, and/or Ni are soluble in suitable solvents that can be suitable and/or are known to those of ordinary skill in the art. Halide, nitrate, and/or carboxylic acid salts of Zn, Ti, Zr, and/or Ni can be suitable. Zinc nitrate $(Zn(NO_3)_2$, available as a hexahydrate from Sigma-Aldrich) is a suitable source of zinc atoms or ions. Zirconyl nitrate $(ZrO(NO_3)_2$, available as a 35% solution in nitric acid from Sigma-Aldrich) is a suitable source of zirconium atoms or ions. Titanium (IV) Oxide Acetylacetonate, $(TiO(acetylacetonate)_2$, (available from Sigma Aldrich), is a suitable source of titanium atoms or ions. Nickel nitrate $(Ni(NO_3)_2$ (available as a hexahydrate from Sigma-Aldrich), is a suitable source of nickel atoms or ions. In most aspects of the methods, water or low molecular weight alcohols, or mixtures thereof can be suitable solvents for this step.

In step "e", the solution comprising M is mixed with the solid $CoMoS_2$, most typically by making a slurry of the solid $CoMoS_2$ with a solution comprising a compound comprising M, although other methods of mixing can be used. In one aspect, catalyst formation can be complete upon mixing, and the slurry only needs to be filtered and carefully dried in order to remove any solvents and fully form and/or isolate the final catalyst composition. In yet other aspects however, additional components, such as a compound comprising K (potassium atoms or ions, such as $K_2CO_3$ or $KNO_3$) can be added during this mixing step, then the final solid product is collected and dried. In some aspects, further chemical treatment, heat treatment, calcining, or other steps could be required to form particular catalysts.

In one aspect, the method further comprises step "f", wherein the catalyst composition is isolated as a solid. In one aspect, this isolation step can be completed by removal of solvents from the solutions, to form a solid comprising the catalyst composition. Furthermore, in many aspects of the methods, the catalyst composition is dried, optionally at a temperature near the boiling point of water at 100° C.

In one aspect of the methods for making the catalyst compositions, calcining in the presence of oxygen or air at high temperatures (such as for example exposing the catalyst composition to a temperature of at least 480° C.), or similar heating under a dry inert gas such as nitrogen, can also be required in order to fully form the catalyst compositions. For example, calcining can result in the conversion of a physical mixture of components to form the catalyst phase, via various chemical reactions, such as for example the removal of some sulfur atoms or ions, and/or the introduction of oxygen atoms or ions into the composition.

In one aspect of the methods for forming the catalyst compositions, mixed metal oxide or sulfide compositions can be contacted with syngas (or other reducing gases such as silanes, etc), often at temperatures above 100° C. Contact with such reducing gases can reduce the solid catalyst compositions and some or all of the metals therein, and/or cause loss or removal of sulfur and oxygen atoms from the solid catalysts.

It is also to be understood that in some aspects of the compositions and methods described herein, once a catalyst has been formed by the methods described above, and the formed catalyst is loaded into reactors and contacted with syngas at reaction temperatures for significant periods of time, some physical and chemical changes can occur in the catalyst, either quickly or over time as the catalytic reactions with syngas are carried out. For example, contact of the metal oxide catalysts described herein with syngas at high temperatures can cause partial or complete "in-situ" reduction of the metal oxides, and such reduction processes can cause removal of sulfur or oxygen atoms from the solid catalyst lattices, and/or cause reduction of some or all of the metal cations present in the catalyst to lower oxidation states, including reduction to metallic oxidation states of zero, thereby producing finely divided and/or dispersed metals on the catalyst supports. Such reduced forms of the catalysts of the invention are within the scope of the described compositions and methods.

It is to be understood that, the catalyst compositions prepared by the above methods and/or steps can comprise $Co_aMo_bS_cM_dO_f$, wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2; and
wherein f is a number determined by the valence requirements of the other elements present in the catalyst.

The possible components and ranges of components for such compositions have already been described above, and can be applied in connection with describing and claiming methods for preparing such compositions.

It should also be understood that in some aspects, the inventions described herein include catalyst compositions prepared by any sequence or combination of the method steps a-f, and any others as described above.

In one aspect, the catalysts formed by reaction steps a-f can also be mixed with or dispersed on supports, fillers, binders, and/or lubricants in order to form a supported or dispersed catalyst composition, by methods well known to those of ordinary skill in the art. Suitable support materials include $Al_2O_3$, $SiO_2$, $TiO_2$, $CeO_2$, $AlPO_4$, $ZrO_2$, silicon-carbide, Molybdenum-carbide, alumino-silicates, zeolites, and molecular sieves, or a mixture thereof, or any of those components separately. Suitable fillers include silicate or alumino-silicate clays, such as bentonite or montmorillonite clays.

Binders are typically inert inorganic oxides or clays that are resistant to the high temperature and other conditions of the processes described herein, but physically bind the zeolite particles together and/or increase their resistance to mechanical attrition. Often, the treated zeolite and the binder are mixed in a liquid solvent, then formed or molded into suitable shapes for catalyst pellets, such as pellets or tablets, then the liquid is removed and the catalyst pellet calcined, via methods known to those of ordinary skill in the art. The binders serve to provide physical integrity and mechanical strength to the catalyst particles. Suitable inorganic binders include alumina, silica, titania, zirconia, or magnesia, and suitable clays including montmorillonite and kaolin clays, and a mixture thereof. In one aspect, the catalyst binder is alumina. In another aspect, the catalyst binder is silica. In yet another aspect, the catalyst binder is titania. In yet another aspect, the catalyst binder is zirconia. In yet another aspect, the catalyst binder is magnesia. In yet another aspect, the catalyst binder is clay.

Lubricants are used to aid the formation of large composite particles or tablets from mixtures of the catalyst composition and supports and/or binders. Suitable lubricants include Sterotex, a powder comprising waxy hydrogenated vegetable oils available from ABITECH of Janesville Wis.

In view of the general descriptions of the preparations of the catalyst compositions and variations thereof that are part of these inventions described above, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

3. Methods for Producing Hydrocarbons from Syngas

Described above are catalysts having the generic formula $Co_aMo_bS_cM_dO_f$, and methods for making those catalysts. Those catalysts are useful for converting mixtures of carbon monoxide and hydrogen (syngas) to hydrocarbons, with unexpectedly high conversions and selectivities, to low molecular weight hydrocarbons such as $C_1$-$C_5$ hydrocarbons.

Also disclosed herein are methods of producing $C_1$-$C_5$ hydrocarbons comprising contacting syngas with a reduced form of a catalyst composition comprising $Co_aMo_bS_cM_dO_f$ wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2;
wherein f is a number determined by the valence requirements of elements of the other elements present in the catalyst composition, and
wherein the method produces $C_1$-$C_5$ hydrocarbons.

The catalyst composition has a formula comprising $Co_aMo_bS_cM_dO_f$ prior to introducing it to conditions suitable for contacting and reacting the catalyst composition with the syngas. Such conditions are known in the art and include high temperatures. The catalyst composition is reduced when present in the conditions associated producing $C_1$-$C_5$ hydrocarbons by contacting the catalyst composition with syngas. Such catalyst composition is referred to herein as a "reduced form of a catalyst composition comprising." A reduction of the catalyst compositions under such conditions is known to those skilled in the art.

In these methods, mixtures of carbon monoxide and hydrogen (syngas) are contacted with suitable catalysts (whose composition, characteristics, and preparation have been already described above and in the Examples below) in suitable reactors and at suitable temperatures and pressures, for a contact time and/or at a suitable space velocity needed in order to convert at least some of the syngas to hydrocarbons. Unexpectedly as compared to methods in the prior art, the methods of the present inventions can be highly selective for the production of $C_1$-$C_5$ hydrocarbons, which are valuable feedstocks for subsequent cracking processes at refineries for producing downstream products, such as low molecular weight olefins.

Methods for producing syngas from natural gas, coal, or waste streams or biomass, at almost any desired ratio of hydrogen to carbon monoxide are well known to those of ordinary skill in the art. A large range of ratios of hydrogen to carbon monoxide can be suitable for the practice of the current invention, but since high conversion of carbon monoxide to hydrocarbons is desired, syngas mixtures comprising at least equimolar ratios of hydrogen to carbon monoxide or higher are typically employed, i.e. from 3:1 $H_2$/CO to 1:1 $H_2$/CO. In some aspects, the ratios of hydrogen to carbon monoxide employed are from 2:1 $H_2$/CO to 1:1 $H_2$/CO. Optionally, inert or reactive carrier gases, such as $N_2$, $CO_2$, methane, ethane, propane, and the like can be contained in and/or mixed with the syngas.

The syngas is typically forced to flow through reactors comprising the solid catalysts, wherein the reactors are designed to retain the catalyst against the vapor phase flow of syngas, at temperatures sufficient to maintain most of the hydrocarbon products of the catalytic reactions in the vapor phase at the selected operating pressures. The catalyst particles can be packed into a fixed bed, or dispersed in a fluidized bed, or in other suitable arrangements known to those of ordinary skill in the art.

In one aspect, the syngas is contacted with the catalyst compositions at a temperature of at least 200° C., or at least 300° C., and at a temperature below 400° C. or from a temperature of 200° C. to 350° C.

In one aspect, the syngas is contacted with the catalyst compositions at a pressure of at least 5 bar, or at least, 10 bar, or at least 15 bar, or at least 25 bar, or at least 50 bar, or at least 75 bar, and less than 200 bar, or less than 100 bar. In many aspects of the methods of the reaction, the syngas is contacted with the catalyst compositions at a pressure from 5 bar to 100 bar.

In one aspect, the syngas is contacted with the catalyst compositions to produce relatively high conversions of the carbon monoxide present in syngas. In one aspect, conversion of carbon monoxide is at least 50%, at least 60%, at least 70%, or at least 80%. In some aspects of the methods, at least 40%, at least 50%, at least 60%, at least 70%, or at least 80% of the syngas is converted to product materials. In one aspect, less than 25%, or less than 20% of the carbon monoxide fed to the reactors is converted to $CO_2$.

In one aspect, the methods of the inventions are unexpectedly highly selective for the production of mixtures of low molecular weight $C_1$-$C_5$ hydrocarbons. Typical $C_1$-$C_5$ hydrocarbons detected in the product include saturated hydrocarbons such as methane, ethane, propanes, butanes, and pentanes, and unsaturated hydrocarbons such as ethylenes, propylenes, butenes, and pentenes. In one aspect, no detectable amounts of hydrocarbons above $C_5$, i.e. $C_6$ or greater hydrocarbons, up to and including hydrocarbon waxes are produced, or can be detected by the analytical methods employed. In one aspect, up to 10%, up to 15%, up to 20%, or up to 25% by weight of $C_1$-$C_5$ alcohols can be produced and/or detected, but in many aspects no $C_1$-$C_5$ alcohols are produced and/or can be detected.

In one aspect, the selectivity for production of propane, including n- and/or iso-propane, from carbon monoxide is greater than 20%, or 30%, 40%, 50%, or 60%. In some aspects of the methods, the selectivity for production of ethane from carbon monoxide is greater than 20%, or 30%, or 40%.

In view of the general descriptions of the catalyst compositions and variations thereof that are part of the inventions described above, herein below are described certain more particularly described aspects of methods for employing the catalysts for converting syngas to hydrocarbons. These particularly recited aspects should not however be interpreted to have any limiting effect on any different claims containing different or more general teachings, or that the "particular" aspects are somehow limited in some way other than the inherent meanings of the language and formulas literally used therein.

4. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

In a particular aspect 1', the invention includes a catalyst composition comprising $$Co_aMo_bS_cM_dO_f,$$

wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2; and
wherein f is a number determined by the valence requirements of the other elements present in the catalyst.

A particular aspect 2' relates to the inventions of aspect 1', wherein M comprises Zn.

A particular aspect 3' relates to the inventions of aspects 1' or 2' wherein M comprises Ti.

A particular aspect 4' relates to the inventions of aspects 1'-3', wherein M comprises Zr.

A particular aspect 5' relates to the inventions of aspects 1'-4', wherein M comprises Ni.

A particular aspect 6' relates to the inventions of aspects 1'-5', wherein b is 1.

A particular aspect 7' relates to the inventions of aspects 1'-6', wherein c is 1.

A particular aspect 8' relates to the inventions of aspects 1'-7', wherein d is from 0.001 to 0.01.

A particular aspect 9' relates to the inventions of aspects 1'-7', wherein d is from 0.004 to 0.01.

A particular aspect 10' relates to the inventions of aspects 1'-9', wherein the catalyst selectively converts syngas to $C_1$-$C_5$ hydrocarbons.

A particular aspect 11' relates to a catalyst composition comprising any one of the catalysts of aspects 1'-10' and a support material.

A particular aspect 12' relates to the inventions of aspect 11', wherein the support material comprises $Al_2O_3$, $SiO_2$, $TiO_2$, $CeO_2$, $AlPO_4$, $ZrO_2$, silicon-carbide, Molybdenum-carbide, an alumino-silicate, a zeolite, or a molecular sieve, or a mixture thereof A particular aspect 13', relates to a method of producing $C_1$-$C_5$ hydrocarbons comprising contacting syngas with a reduced form of the catalyst of any one of aspects 1'-12', thereby producing $C_1$-$C_5$ hydrocarbons.

A particular aspect 14' relates to the methods of aspect 13', wherein the selectivity for production of propane is greater than 20%.

A particular aspect 15' relates to the methods of aspect 13', wherein the selectivity for production of propane is greater than 50%.

A particular aspect 16' relates to the methods of aspects 13'-15', wherein the selectivity for production of ethane is greater than 20%.

A particular aspect 17' relates to the methods of aspects 13'-15', wherein the selectivity for production of ethane is greater than 40%.

A particular aspect 18' relates to the methods of aspects 13'-17', wherein the method does not produce $C_1$-$C_5$ alcohols.

A particular aspect 19' relates to the methods of aspects 13'-18', wherein the method does not produce wax.

A particular aspect 20' relates to the methods of aspects 13'-19', wherein the method does not produce hydrocarbons above $C_5$.

A particular aspect 21' relates to the methods of aspects 13'-20', wherein the method is performed at a temperature of at least 200° C.

A particular aspect 22' relates to the methods of aspects 13'-20', wherein the method is performed at a temperature of 200° C. to 350° C.

A particular aspect 23' relates to the methods of aspects 13'-20', wherein the method is performed at a temperature of at least 300° C.

A particular aspect 24' relates to the methods of aspects 13'-23', the method is performed at a pressure of at least 25 bar.

A particular aspect 25' relates to the methods of aspects 13'-23', wherein the method is performed at a pressure of 25 bar to 85 bar.

A particular aspect 26' relates to the methods of aspects 13'-23', wherein the method is performed at a pressure of at least 75 bar.

A particular aspect 27' relates to the methods of aspects 13'-26', wherein the method converts at least 40% of the syngas.

A particular aspect 28' relates to the methods of aspects 13'-27', wherein the method produces less than 25% $CO_2$ by weight.

A particular aspect 29' method of preparing a catalyst comprising the steps of:
a) providing a solution comprising Mo and S;
b) providing a solution comprising Co;
c) mixing the solution comprising Mo and S with the solution comprising Co, thereby forming $CoMoS_2$;
d) providing a solution comprising M, wherein M comprises Zn, Ti, Zr, or Ni, or a mixture thereof; and
e) mixing the solution comprising M with the $CoMoS_2$, to produce a catalyst.

A particular aspect 30' relates to the invention of aspect 29', wherein the solution comprising Mo and S comprises a salt of $MoS_4^{2-}$.

A particular aspect 31' relates to the invention of aspect 29', wherein the solution comprising Mo and S comprises $(NH_4)_2MoS_4$.

A particular aspect 32' relates to the inventions of aspect 29'-31', wherein the solution comprising Co comprises $Co(CH_3CO_2)_2$.

A particular aspect 33' relates to the inventions of aspects 29'-32', wherein mixing the solution comprising $MoS_4$ with the solution comprising Co comprises simultaneously adding the solution comprising $MoS_4$ and with the solution comprising Co to aqueous acetic acid.

A particular aspect 34' relates to the inventions of aspects 29'-33', wherein the method further comprises drying the $CoMoS_2$.

A particular aspect 35' relates to the inventions of aspects 29'-34', wherein the solution comprising M comprises a salt of Zn, Ti, Zr, or Ni, or a mixture thereof.

A particular aspect 36' relates to the inventions of aspects 29'-35', wherein the solution comprising M comprises zirconyl nitrate.

A particular aspect 37' relates to the inventions of aspects 29'-36', wherein the solution comprising M comprises zinc nitrate.

A particular aspect 38' relates to the inventions of aspects 29'-37', wherein the solution comprising M comprises titanium oxide acetylacetonate.

A particular aspect 39' relates to the inventions of aspects 29'-38', wherein the method further comprises preparing a catalyst composition by mixing the catalyst with a support.

A particular aspect 40' relates to the inventions of aspects 29'-39', wherein the method further comprises preparing a catalyst composition by mixing the catalyst with a lubricant.

A particular aspect 41' relates to the invention of aspect 40', wherein the lubricant comprises a vegetable oil powder.

A particular aspect 42' relates to the inventions of aspects 29'-41', wherein the method further comprises mixing the catalyst with a binder.

A particular aspect 43' relates to the inventions of aspects 29'-42', wherein the method further comprises mixing the catalyst with a filler.

A particular aspect 44' relates to the invention of aspect 43', wherein the filler comprises bentonite clay.

A particular aspect 45' relates to the inventions of aspects 29'-44', wherein the method further comprises mixing the catalyst with a compound comprising K.

A particular aspect 46' relates to the inventions of aspect 45', wherein the compound comprising K comprises $K_2CO_3$ or $KNO_3$.

A particular aspect 47' relates to the inventions of aspects 29'-46', wherein the catalyst composition is calcined in the presence of oxygen.

A particular aspect 48' relates to the inventions of aspects 29'-47', wherein the method further comprises isolating the catalyst as a solid.

A particular aspect 49' relates to catalyst composition prepared by any of the methods of aspects 29'-48'.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

1. Example 1—Preparation of $CoMoS_2$ (Catalyst Starting Material)

A solution of $(NH_4)_2MoS_4$ was prepared by dissolving ammonium molybdate tetrahydrate [$(NH_4)_6Mo_7O_{24}$ $4H_2O$] (15 g) into ammonium sulfide [$(NH_4)_2S/H_2O$] (106 ml, 20%) with stirring (340-343K, 1 h). A solution of the cobalt compound was prepared by dissolving cobalt acetate [Co$(CH_3CO_2)_2$] (10.5 g) in distilled water (200 ml). The two solutions were then added simultaneously drop-wise into a well-stirred solution of aqueous acetic acid solution (30%) at 328 K. The solution was vigorously stirred (1 h, 328 K) and the resultant black solution was filtered and dried at room temperature in a fume cupboard overnight. The resulting slurry was dried at 110° C. for 16 h. The dried sample was heated under nitrogen (1 h, 773 K ramping rate 25 K/min), giving a grey-black product, $CoMoS_2$. This product was then ground and mixed with $K_2CO_3$, bentonite clay and Sterotex® lubricant in a weight ratio of 66 catalyst: 10 $K_2CO_3$: 20 bentonite: 4 Sterotax® and tested under standard conditions described elsewhere herein.

2. Example 2—Preparation of a Supported Catalyst Comprising $CoMoSZr_{0.0048}$

A solution of $(NH_4)_2MoS_4$ was prepared by dissolving ammonium molybdate tetrahydrate [$(NH_4)_6Mo_7O_{24}$-$4H_2O$] (15 g) into ammonium sulfide [$(NH_4)_2S/H_2O$] (106 ml, 20%) with stirring (340-343 K, 1 h). A solution of the cobalt compound was prepared by dissolving cobalt acetate [Co$(CH_3CO_2)_2$] (10.5 g) in distilled water (200 ml). The two solutions were then added simultaneously drop-wise into a well-stirred solution of aqueous acetic acid solution (30%) at 328 K. The solution was vigorously stirred (1 h, 328 K) and the resultant black solution of $CoMoS_2$ was filtered and dried at room temperature in a fume cupboard overnight.

0.0506 g of zirconyl nitrate was dissolved in 6.7 ml of distilled water was added into 10 g of the $CoMoS_2$ until it was in a moldable form that was intermediate between a paste and a solution state. The resulting slurry was dried at 110° C. for 16 h. The dried sample was heated under nitrogen (1 h, 773 K ramping rate 25 K/min)/giving a grey-black product.

This product solid was then ground and mixed with $K_2CO_3$, bentonite clay and Sterotex® lubricant (a hydrogenated vegetable oil available from AIC of Framingham Mass.), in a weight ratio of 66 catalyst: 10 $K_2CO_3$: 20 bentonite: 4 Sterotax® and tested under standard catalytic conditions described below.

3. Example 3—Preparation of a Supported Catalyst Comprising $CoMoSZn_{0.0065}$

A solution of $(NH_4)_2MoS_4$ was prepared by dissolving ammonium molybdate tetrahydrate [$(NH_4)_6Mo_7O_{24}4H_2O$] (15 g) into ammonium sulfide [$(NH_4)_2S/H_2O$] (106 ml, 20%) with stirring (340-343K, 1 h). A solution of the cobalt compound was prepared by dissolving cobalt acetate [Co$(CH_3CO_2)_2$] (10.5 g) in distilled water (200 ml). The two solutions were then added simultaneously drop-wise into a well-stirred solution of aqueous acetic acid solution (30%) at 328 K. The solution was vigorously stirred (1 h, 328 K) and the resultant black solution was filtered and dried at room temperature in a fume cupboard overnight.

0.097 g of zinc nitrate dissolved in 6.7 ml of distilled water was added into 10 g of $CoMoS_2$ until it was in a moldable form between paste and solution state. The resulting slurry was dried at 110° C. for 16 h. The dried sample was heated under nitrogen (1 h, 773 K ramping rate 25 K/min), giving a grey-black product.

This product was then ground and mixed with $K_2CO_3$, bentonite clay and Sterotex® lubricant in a weight ratio of 66 catalyst: 10 $K_2CO_3$: 20 bentonite: 4 Sterotax® and tested under standard conditions described elsewhere herein.

4. Example 4—Preparation of a Supported Catalyst Comprising $CoMoSTi_{0.0092}$

A solution of $(NH_4)_2MoS_4$ was prepared by dissolving ammonium molybdate tetrahydrate [$(NH_4)_6Mo_7O_{24}4H_2O$] (15 g) into ammonium sulfide [$(NH_4)_2S/H_2O$] (106 ml, 20%) with stirring (340-343 K, 1 h). A solution of the cobalt compound was prepared by dissolving cobalt acetate [Co$(CH_3CO_2)_2$] (10.5 g) in distilled water (200 ml). The two solutions were then added simultaneously drop-wise into a well-stirred solution of aqueous acetic acid solution (30%) at 328 K. The solution was vigorously stirred (1 h, 328 K) and the resultant black solution was filtered and dried at room temperature in a fume cupboard overnight.

0.109 g of Titanium (IV) Oxide Acetylacetonate dissolved in 6.7 ml of acetone was added into 10 g of CoMoS$_2$ until it was in a moldable form between paste and solution state. The resulting slurry was dried at 110° C. for 16 h.

This product was then ground and mixed with K$_2$CO$_3$, bentonite clay and Sterotex® lubricant in a weight ratio of 66 catalyst: 10 K$_2$CO$_3$: 20 bentonite: 4 Sterotax® and tested under standard catalytic conditions.

5. Example 5—Catalyst Testing Experiments

The catalysts of Examples 1-4 were used. Catalytic test experiments for the conversion of syngas to hydrocarbons were carried out using a fixed bed micro reactor. The dilution of catalyst was performed by intimate mixing of the catalyst with silicon carbide (4.8 ml catalyst/5.2 ml silicon carbide for Co-MoS$_2$ based catalyst).

Prior to the catalytic run, after the micro reactor had been loaded with catalyst, a system leakage test was carried out using nitrogen. After the system was found safe and leak-free, syngas (1:1 ratio of H$_2$/CO) was gradually introduced to the system, replacing the nitrogen. Following the complete replacement, the system was brought up to the required pressure, followed by heating with a ramping rate of 1 K/min until it reached the desired temperature. All catalysts were studied under identical reaction conditions. Reaction pressure was 75 bar and temperature of reaction was 580 K. The reaction was continued for 80-200 hours and the products were separated and analyzed by gas chromatography. Longer chain alcohols were collected in a liquid trap.

Results of the catalytic experiments are reproduced in Table 1 below.

TABLE 1

Data showing performance of disclosed catalysts ( 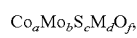

| | Source of Catalyst - Example | | | |
|---|---|---|---|---|
| | 1 (comparative) | 2 | 3 | 4 |
| Catalyst | CoMoS$_2$ | CoMoSZr$_{0.0048}$ | CoMoSZn$_{0.0065}$ | CoMoSTi$_{0.0092}$ |
| Conversion of CO (CO$_{in}$ − (CO$_{out}$/CO$_{in}$) * 100%) (wt %) | 48.5 | 78 | 92 | 65 |
| CO$_2$ (wt %) | 35.5 | 3 | 7.5 | 21 |
| Methane (wt %) | 9 | 22.7 | 36.8 | 35.54 |
| Ethylene (wt %) | 0.2 | 1 | 1.5 | 0.01 |
| Ethane (wt %) | 5.0 | 25 | 4.8 | 45.56 |
| Propylene (wt %) | 2.5 | 0.5 | 0.25 | 0.83 |
| Propane (wt %) | 11.5 | 23 | 55.1 | 17.57 |
| Butylenes (wt %) | 1.8 | 2.6 | 0.26 | 0.08 |
| Butane (wt %) | 5.0 | 1.9 | 1.29 | 0.41 |
| Alcohols (C1-C5) (wt %) | 65 | 23.3 | 0 | 0 |
| total product (wt %) | 100.0 | 100.0 | 100.0 | 100.0 |

As is clear from the table, that disclosed catalysts promoted syngas conversion while decreasing yields of CO$_2$ and alcohols, while dramatically increasing the selectivity for C$_1$-C$_5$ hydrocarbons, especially methane, ethane, and propane. No production of C$_6$ or higher alkanes or waxes was detected.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A catalyst for selective synthesis of lower hydrocarbons from syngas comprising elements with the relative molar ratios represented by the formula $$Co_aMo_bS_cM_dO_f,$$

wherein a is 1;
wherein b is from 0.8 to 1.2;
wherein c is from 1 to 2;
wherein M comprises Zn, Ti, Zr, or Ni, or a mixture thereof,
wherein d is from 0.000001 to 0.2; and
wherein f is a number determined by the valence requirements of the other elements present in the catalyst,
wherein the lower hydrocarbons are selected from the group consisting of methane, ethane, and propane, or a mixture thereof.

2. The catalyst of claim 1, wherein M comprises Zn.
3. The catalyst of claim 1, wherein M comprises Ti.
4. The catalyst of claim 1, wherein M comprises Zr.
5. The catalyst of claim 1, wherein M comprises Ni.
6. The catalyst of claim 1, wherein b is 1.
7. The catalyst of claim 1, wherein c is 1.
8. The catalyst of claim 1, wherein d is from 0.001 to 0.01.
9. A catalyst composition comprising the catalyst of claim 1 and a support material.
10. The catalyst composition of claim 9, wherein the support material comprises Al$_2$O$_3$, SiO$_2$, TiO$_2$, CeO$_2$, AlPO$_4$, ZrO$_2$, silicon-carbide, Molybdenum-carbide, an alumino-silicate, a zeolite, or a molecular sieve, or a mixture thereof.
11. A method of producing C1-C5 hydrocarbons comprising contacting syngas with a reduced form of the catalyst of claim 1, thereby producing C1-C5 hydrocarbons.

12. The method of claim 11, wherein the selectivity for production of propane is greater than 50%.

13. The method of claim 11, wherein the selectivity for production of ethane is greater than 40%.

14. The method of claim 11, wherein the method does not produce C1-C5 alcohols.

15. The method of claim 11, wherein the method is performed at a pressure of 25 bar to 85 bar.

16. The method of claim 11, wherein the method converts at least 40% of the syngas.

17. The method of claim 11, wherein the method produces less than 25% $CO_2$ by weight.

18. A method of preparing a catalyst comprising the steps of:
   a) providing a solution comprising Mo and S;
   b) providing a solution comprising Co;
   c) mixing the solution comprising Mo and S with the solution comprising Co, thereby forming $CoMoS_2$;
   d) providing a solution comprising M, wherein M comprises Zn, Ti, Zr, or Ni, or a mixture thereof; and
   e) mixing the solution comprising M with the $CoMoS_2$, to produce a catalyst wherein the catalyst comprises elements with the relative molar ratios represented by the formula $$Co_aMo_bS_cM_dO_f,$$

wherein a is 1;
   wherein b is from 0.8 to 1.2;
   wherein c is from 1 to 2;
   wherein M comprises Zn, Ti, Zr, or Ni, or a mixture thereof,
   wherein d is from 0.000001 to 0.2; and
   wherein f is a number determined by the valence requirements of the other elements present in the catalyst.

19. The method of claim 18, wherein the solution comprising Mo and S comprises a salt of $MoS_4^{2-}$.

20. A composition comprising syngas and a catalyst comprising elements with the relative molar ratios represented by the formula $$Co_aMo_bS_cM_dO_f,$$

wherein a is 1;
   wherein b is from 0.8 to 1.2;
   wherein c is from 1 to 2;
   wherein M comprises Zn, Ti, Zr, or Ni, or a mixture thereof,
   wherein d is from 0.000001 to 0.2; and
   wherein f is a number determined by the valence requirements of the other elements present in the catalyst.

* * * * *